US008652799B2

(12) United States Patent
Bellemare et al.

(10) Patent No.: US 8,652,799 B2
(45) Date of Patent: Feb. 18, 2014

(54) METHOD OF DETECTING BIOACTIVE MOLECULES IN A FLUID SAMPLE

(75) Inventors: François Bellemare, Trois-Rivières (CA); Lucie Lorrain, Champlain (CA); Nathalie Boucher, Trois-Rivières (CA)

(73) Assignee: Labbell Inc., Trois-Rivières (CA)

( * ) Notice: Subject to any disclaimer, the term of this patent is extended or adjusted under 35 U.S.C. 154(b) by 0 days.

(21) Appl. No.: 13/055,332

(22) PCT Filed: Jul. 31, 2008

(86) PCT No.: PCT/CA2008/001392
§ 371 (c)(1), (2), (4) Date: Apr. 11, 2011

(87) PCT Pub. No.: WO2010/012063
PCT Pub. Date: Feb. 4, 2010

(65) Prior Publication Data

US 2011/0177546 A1 Jul. 21, 2011

(51) Int. Cl.
*C12Q 1/02* (2006.01)

(52) U.S. Cl.
USPC .......... 435/29

(58) Field of Classification Search
None
See application file for complete search history.

(56) References Cited

U.S. PATENT DOCUMENTS 6,964,857 B2 * 11/2005 Greenbaum et al. .......... 435/29

FOREIGN PATENT DOCUMENTS

| | | | |
|---|---|---|---|
| DE | 19910436 | | 10/2000 |
| EP | 242225 B1 | * | 11/1993 |
| WO | WO 2004/046717 A1 | | 6/2004 |
| WO | 2008/001392 | | 7/2008 |
| WO | 2008/001392 | | 2/2011 |

OTHER PUBLICATIONS

Macfie et al., The Cell Wall as a Barrier to Uptake of Metal Ions in the Unicellular Green Alga *Chlamydomonas reinhardtii* (Chlorophyceae), 2000, Arch. Env. Contam. Toxicol. 39: 413-419.*
LuminoTox™ SAPS Test Kit Environmental Technology Verification Report, 2006, U.S. Environmental Protection Agency, pp. 1-35.*
Naessens et al., Fiber Optic Biosensor Using *Chlorella vulgaris* for Determination of Toxic Compounds, 2000, Ecotoxicology and Environmental Safety 46, 181-185 (2000).*
Vedrine et al., Optical whole-cell biosensor using *Chlorella vulgaris* designed for monitoring herbicides, Biosensors and Bioelectronics 18: 457-463 (2003).*
Bengtson Nash et al., The selection of a model microalgal species as biomaterial for a novel aquatic phytotoxicity assay, 2005, Aquatic Toxicology 72: 315-326.*
Sanders et al., Stand-off tissue-based biosensors for the detection of chemical warfare agents using photosynthetic fluorescence induction, 2001, Biosensors & Bioelectronics 16: 439-446.*
Schreiber et al., New type of dual-channel PAM chlorophyll fluorometer for highly sensitive water toxicity biotests, 2002, Photosynthesis Research 74: 317-330.*
Bellemare, Francois et al., Combined Use of Photosynthetic Enzyme Complexes and Microalgal Photosynthetic Systems for Rapid Screening of Wastewater Toxicity, Env. Toxicol., (2006), 21: 445-449.
Comite Federal-Provincial-Territorial Sur L'Eau Potable, Recommandations pour la qualité de l'eau potable au Canada, published on line in Wiley InterScience, Canada (2007), pp. 1-15.
Federal-Provincial-Territorial Committee on Drinking Water, Guidelines for Canadian Drinking Water Quality, published on line in Wiley InterScience, Canada (2010), pp. 1-15.
Rouillon, Regis et al., Amperometric activity measurements of photosynthetic material immobilized in poly (vinylalcohol)-SbQ. Application to detect pollutants. Current Topics in Electrochemistry, (2000), 7: 125-133.
Laberge, Denise et al., In vitro phytotoxicity screening test using immobilized spinach thylakoids. Environmental Toxicology and Chemistry, (1999), 18(12): 2851-2858.
Supplementary Euroopean Search Report issued in EP 08 78 3303 on Nov. 16, 2011.
Brack W. et al., "Chlorophyll A fluorescence: a tool for the investigation of toxic effects . . . ", (1998), Ecotoxicology and Environmental, Safety, vol. 40, No. 1-2: 34-41.
Chul-Woong Cho et al., "Microalgal photosynthetic activity measurement system for rapid toxicity assessment", (2008), Ecotoxicology, vol. 17, No. 6: 455-463.
Conrad R. et al., "Changes in Yield of in-vivo fluorescence of chlorophyll A as a tool . . . ", (1993), Journal of Applied Phycology, vol. 5, No. 5: 505-516.
Weston L.H. et al., "Detection and quantification of triazine herbicides using algal cell fluorescence", (1991), Biotechnology Techniques, vol. 5, No. 5: 327-330.

* cited by examiner

*Primary Examiner* — Jon P Weber
*Assistant Examiner* — Robert Yamasaki
(74) *Attorney, Agent, or Firm* — Goudreau Gage Dubuc; Julie Gauvreau

(57) ABSTRACT

A method of detecting the presence of bioactive molecules in a fluid sample, comprising contacting a solution of a microorganism selected from the group consisting of a monocellular algae and a cyanobacteria with the fluid sample so as to obtain a formulation having a microorganism concentration of 200 000-$1\times10^7$ cells/mL of fluid sample; incubating the formulation for 10 to 120 minutes at a pH of 7 to 12 and a temperature between 18 and 35° C.; and measuring the fluorescence emitted by the formulation, whereby a fluorescence emitted in the sample that is lower than that in a control sample is an indication that the sample contains a bioactive molecule.

33 Claims, 17 Drawing Sheets

Pb detection in 15 minutes with different mix of [Cu+Cd]

control test : the solution identified on the *y* axis :
- Distilled water serves as blank
- Cu 0,1 ppm + Cd 0,5 ppm
- Cu 0,1 ppm + Cd 1ppm
- Cu 0,25 ppm + Cd 1 ppm
- Cd ppm
- Cu 0,1 ppm
- Cu 0,25 ppm

Pb analysis
the mixture indicated in *y* axis serves as blank solution

Pb detection in 60 minutes with different mix of [Cu+Cd]

METHOD OF DETECTING BIOACTIVE MOLECULES IN A FLUID SAMPLE

CROSS REFERENCE TO RELATED APPLICATIONS

This application is a National Entry Application of PCT application no. PCT/CA2008/001392 filed on Jul. 31, 2008 and published in English under PCT Article 21 (2) The document above is incorporated herein in its entirety by reference.

FIELD OF THE INVENTION

The present invention relates to methods of detecting bioactive molecules in a fluid sample.

BACKGROUND OF THE INVENTION

On a global scale, pathogenic contamination of drinking water represents the most significant risk to humans. However, significant risks to human health may also result from exposure to non pathogenic, toxic chemical contaminants that are omnipresent in waters from which drinking water is derived. The chemical contamination of streams and water sources has become an important fate since many of the chemicals that compromise the health of aquatic ecosystems have the potential to compromise human health.

In international publication no. WO 2004/046717 A1, the content of which is herein incorporated by reference in its entirety, photosynthesis-based biosensors and bioassays were disclosed for detecting toxic molecules in fluids and methods and kits for using the same.

It is known that inhibition of photosynthesis by different pollutants (inhibitors) may change a plant's physiological state (Papageorgiou, 1975; Govindjee, 1995; Krause G. H. and Weis E. 1991). Therefore, plant biochemical parameters linked to photosynthesis, such as ATP-formation, $CO_2$ fixation and $O_2$ evolution, have been used in the past as indicators of toxicity induced by pollutants (Samson and Popovic, 1990; Pascal and Popovic, 1993; Laberge et al., 1999; Rouillon et al., 2000). The complexity of these methods and the time required to obtain results with them make them rather inconvenient as tools in environmental toxicology.

Using photosynthetic algae rather than thylakoids enables the detection of bioactive molecules acting on metabolisms other than photosynthesis that can be indirectly measured through photosynthetic activity (Organophosphorus, antibiotics, amines, etc.).

Methods of the prior art using algae to detect contaminants required up to 7 days of incubation.

The present invention refers to a number of documents, the content of which is herein incorporated by reference in their entirety.

SUMMARY OF THE INVENTION

The present invention advantageously uses whole microorganisms such as monocellular algae and cyanobacteria. In specific embodiments, they enable the detection of contaminants within a maximum of 60 minutes of incubation with or without adjuvants.

Adjuvants may modify the charge of bioactive molecules, membrane permeability, the algae physiological state and/or certain other metabolisms directly or indirectly affecting photosynthetic activity. For instance, the pH modifies the charge of bioactive molecules; the temperature affects the cell permeability; exposition to light or darkness during incubation affects the physiological state of the algae, the addition of organic molecules (such as atrazine or tetracycline) and/or inorganic molecules (such as metallic ions) in the reaction media affects the algae metabolism and the use of the lowest possible concentration of algae optimizes sensitivity of the assay. Adjuvants behave differently depending on the algae species used. In particular, the composition of cell membranes and walls varies with the type of microorganism used, and this variation confers these microorganisms a specificity and/or a higher sensitivity to certain bioactive molecules.

Many bioactive molecules such as POPs (persistent organic pollutants), insecticides and antibiotics, do not directly affect the photosynthetic process or directly affect it but with more difficulty because they cannot easily cross the cell wall and membrane. In algae and other microorganisms, the bioactive molecules interfere with other cell metabolisms such as growth, and cell cycle, motility, respiration, nutrient uptake, nucleic acid and protein synthesis. The Applicant determined that such interference with other cell metabolisms also has an inhibitory effect, although indirect, on photosynthetic activity. By selecting the most sensitive algal species, modifying the permeability of the cell wall (for bioactive metals for instance) and membrane (by modifying the pH, temperature, ions, using chemicals known as cell membrane permeants), the physiological state of the algae by light and dark conditions, the cell concentration, the cell growth, the inclusion of additives into the reaction medium, the effect (direct or indirect) of bioactive molecules on the photosynthetic activity will be emphasized and/or accelerated.

More specifically, in accordance with the present invention, there is provided a method of detecting the presence of bioactive molecules in a fluid sample, comprising contacting a solution of a microorganism selected from the group consisting of a monocellular algae and a cyanobacteria with the fluid sample so as to obtain a formulation having a microorganism concentration of 200 000-$1\times10^7$ cells/mL of fluid sample; incubating the formulation for 10 to 120 minutes at a pH of 7 to 12 and a temperature between 18 and 35° C.; and measuring the fluorescence emitted by the formulation, whereby a fluorescence emitted in the sample that is lower than that in a control sample is an indication that the sample contains a bioactive molecule.

In a specific embodiment, the incubation is performed under ambient light. In another specific embodiment, the incubation under ambient light is followed by an incubation under green light or darkness. In another specific embodiment, the incubation under green light or darkness has a duration of about to about 35 minutes. In another specific embodiment, the incubation under green light or darkness has a duration of about 15 minute. In another specific embodiment, the incubation pH is between about 4 and 12. In another specific embodiment, the incubation pH is between about 11 and 12. In another specific embodiment, the microorganism solution was activated under ambient light prior to the incubation step. In another specific embodiment, the formulation further comprises an additive. In another specific embodiment, the additive is cadmium. In another specific embodiment, the additive is $H_2O_2$. In another specific embodiment, the additive is copper. In another specific embodiment, the additive is cadmium and copper.

In another specific embodiment, the microorganism is a Chlorophyceae. In another specific embodiment, the microorganism is a fresh water Chlorophyceae. In another specific embodiment, the microorganism is *Chlorella vulgaris*. In another specific embodiment, the incubation temperature is about 35° C. In another specific embodiment, the microorganism solution was activated under ambient light for at least 90 minutes prior to the incubation step. In another specific embodiment, the microorganism cellular concentration is between about $2.5\times10^6$ and $5\times10^6$ cells/mL of aqueous solution. In another specific embodiment, the microorganism cellular concentration is about $2.5\times10^6$ cells/mL of aqueous solution. In another specific embodiment, the bioactive molecule is selected from the group consisting of atrazine, diuron, glyphosate, chlorpyriphos, copper, lead, cadmium, mercury, cyanides, tetracycline, zinc, nickel and ammoniacal nitrogen.

In another specific embodiment, the microorganism is *Ankistrodesmus falcatus*. In another specific embodiment, the microorganism is *Monoraphidium arcuatum*. In another specific embodiment, the microorganism is *Scenedesmus quadricauda*. In another specific embodiment, the microorganism is *Desmosdesmus subspicatus*. In another specific embodiment, the microorganism is *Scenedesmus subpicatus*. In another specific embodiment, the microorganism is *Scenedesmus obliquus*. In another specific embodiment, the microorganism is *Pseudokirchneriella subspicata*. In another specific embodiment, the microorganism is *Chlamydomonas reinhardtii*.

In another specific embodiment, the microorganism is a marine Chlorophyceae. In another specific embodiment, the microorganism is *Dunalliela tertiolecta*. In another specific embodiment, the *Dunalliela tertiolecta* cellular concentration is between about 200 000 and 350 000 cells/mL aqueous solution. In another specific embodiment, the *Dunalliela tertiolecta* solution was activated under ambient light for at least 45 minutes prior to the incubation step. In another specific embodiment, the bioactive molecule is selected from the group consisting of atrazine, diuron, glyphosate, malathion, chlorpyriphos, progesterone and dicrotophos.

In another specific embodiment, the microorganism is a cyanobacteria. In another specific embodiment, the cyanobacteria is *Anabaena* sp. In another specific embodiment, the cyanobacteria solution was activated under ambient light for at least 60 minutes prior to the incubation step. In another specific embodiment, the microorganism is *Nostoc commune*. In another specific embodiment, the microorganism is *Phaeodactylum tricornutum*. In another specific embodiment, In another specific embodiment, the microorganism is *Nitzchia clostridium*. In another specific embodiment, the microorganism is *Lasallia pustulata*. In another specific embodiment, the microorganism is *Zostera caprocorni.*

Definitions:

A "basic pH" is defined herein as a pH of 7.8 or higher

A "bioactive molecule" is defined herein as a molecule that indirectly or directly (e.g. Atrazine) affects (activate or inhibit) the photosynthetic activity of algae and cyanobacteria. Without being so limited, such molecules include antibiotics such as tetracycline, hormones such as progesterone, pesticides such as triazines, urea, organophosphorus, and carbamates; metallic ions such as cadmium, copper, chromium, zinc, lead, mercury, etc.; analgesic such as acetylsalicylic acid, antidepressor such as paroxetine, stimulants such as nicotine and caffeine and other drugs.

An "initial cellular concentration" is defined herein as the concentration of the cells in the sample prior to any treatment.

As used herein, the term "room temperature" is meant to refer to a temperature between about 18 to about 25° Celsius.

As used herein, the term "additive" refers to a substance or a mixture of substances that can be used in accordance with specific embodiments of the present invention for its ability to inhibit certain metabolisms of microorganisms such as algae and cyanobacteria, which inhibition directly or indirectly affects/inhibits the microorganism's photosynthetic activity. An additive is used in the present invention to increase the detectability of bioactive molecules in assays of the present invention. Without being so limited, such additive include copper, cadmium, chlorpyriphos, phenylureas, triazine, nickel, chromium, $H_2O_2$ or a combination thereof.

As used herein, the term "monocellular algae" includes, without being so limited the species *Desmosdesmus subspicatus, Ankistrodesmus falcatus, Chlorella vulgaris, Monoraphidium arcuatum, Scenedesmus quadricauda, Scenedesmus subpicatus, Pseudokirchneriella subspicata, Dunaliella tertiolecta, Phaeodactylum tricornutum, Scenedesmus obliquus, Chlamydomonas reinhardtii, Lasallia pustulata, Zostera caprocorni* and *Nitchia clostridium.*

As used herein, the term "cyanobacteria" refers to cyanophyceae including those of the ocillatoriales order, including the spirulina, and including those of the nostocales order, including the *anabaena* genus and the *Nostoc commune* genus.

As used herein, the term "ambient light" is meant to refer to any day light or artificial light such as that produced by a fluorescent lamp or incandescent lamp. Excessive temperature would kill the algae or cyanobacteria. Hence *Chlorella vulgaris* can optimally grow at a temperature of up to 30° C., whereas *Dunaliella tertiolecta* and *nabaena* sp. can optimally grow at a temperature of up to 25° C. Accordingly, the light is advantageously fluorescent (that does not produce heat) or controllable to avoid excessive heating. A temperature lower than optimal will simply slow growth. In addition, luminosity has an impact on algae and cyanobacteria growth. Hence green algae are advantageously grown in at a luminosity of up to 3500 Lux, whereas *Anabaena* tolerates a luminosity of up to about 1000 lux. Luminosity is not believed to have an impact on incubation, however.

Although the culture medium used in the Examples herein are BBM, f/2 and BG11, any other culture medium appropriate for culturing monocellular algae and cyanobacteria of the methods of the present invention may be used. In particular, any culture medium recommended by any appropriate authority such as the University of Toronto Cell Culture (UTCC), the Global Bioresource Center in ATCC, the Culture Collection of Algae and Protozoa (CCAP) in Scotland and the Culture Collection of Algae at the University of Texas at Austin (UTEX) can be used.

Although a stabilization of microorganisms usable in the present invention is advantageous for storage and sale, it is not necessary in the assays of the present invention per se. Indeed, as may be seen in Examples below, non stabilized microorganisms yield useful results in accordance with the present invention.

A "sample" is defined herein as any fluid containing toxic molecules. Without being so limited, it includes surface water, ground water, storm water, underground water, drinking water, agricultural effluents, industrial effluents (pulp and paper, municipal waste water, waste water landfills leachates, textile, petrochemical, chemical, mining), water extracted from food, sludge, sediments and scories.

The terminology "toxic" and "toxicity" refers herein to the property of a substance enabling it to disrupt (inhibit or enhance) in part or in whole the photosynthetic efficiency of monocellular algae and cyanobacteria.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

Figure 1:
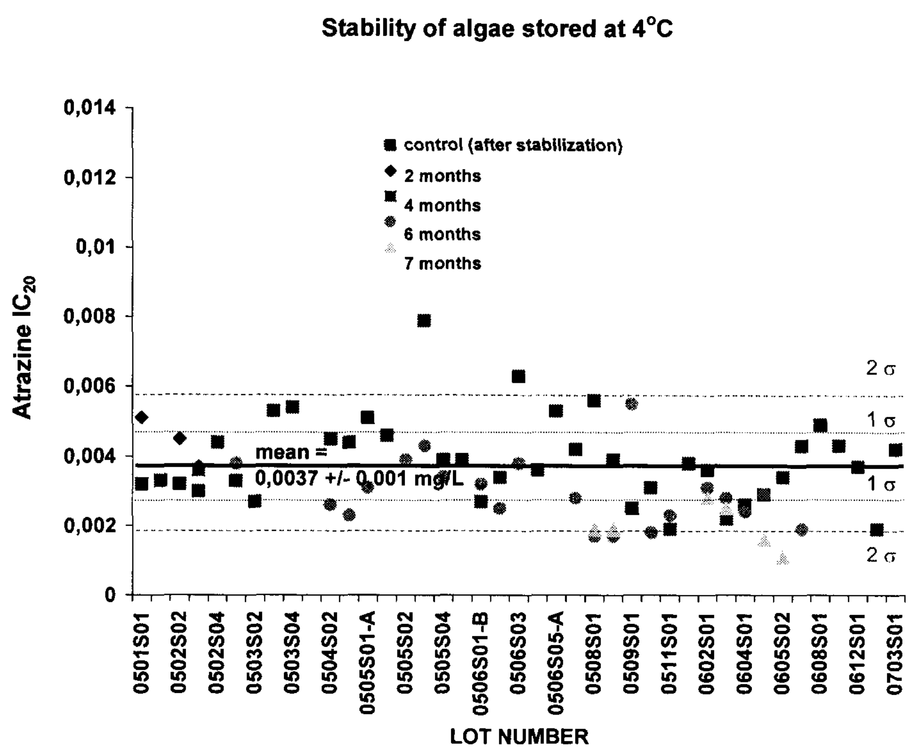
FIG. 1 demonstrates the stability of *Chlorella vulgaris* at 4° C.

With specific embodiments of the methods of the present invention, chemical bioactive molecules inhibiting constituents of the photosynthetic transport chain can be detected within about 15 minutes. The use of a whole microorganism such as the green algae *Chlorella vulgaris* provides the detection of specific D1 protein herbicide inhibitors, namely atrazine and diurion within about 10 minutes, atrazine threshold being 0.0007 ppm and diuron threshold being lower than 0.0005 ppm. The stabilized *Chlorella vulgaris* can be kept 4 and 6 months at 20° C. and 4° C., respectively.

The present invention also concerns a method for ammonia nitrogen detection comprising changing algal cell permeability. This compound is detected at 100 ppm at neutral pH but the increment of pH up to 11 decreases the threshold to 1 ppm. Algal permeability can also be modified by increasing the incubation temperature of the assay. For example, fluorescence emission is inhibited in 15 minutes by copper ions, tetracycline and progesterone if *Chlorella vulgaris* is incubated at 35° C., while at room temperature the detection of these compounds in 15 minutes was possible when these compounds are present at higher concentrations. *Chlorella vulgaris* is a freshwater alga and is used for freshwater monitoring while *Dunaliella tertiolecta* is used of for marine water monitoring.

In specific embodiments, the measure of the fluorescence emitted by the photosynthetic organisms is conducted as described in WO 2004/046717 to Bellemare et al. published Jun. 3, 2004. $F_0$ corresponds to the minimal fluorescence of the activated photosystems. This fluorescence is produced by a weak illumination of the photosystems. $F_1$ corresponds to an illumination slightly higher than $F_0$. $F_2$ (near maximal fluorescence level) corresponds to the fluorescence induced by strong/actininc illumination.

In specific embodiments, a fluorometer continuously but weakly illuminates the photosystems with a light emitting diode (LED) emitting light at a wavelength of 475 nm, 605 nm or 660 nm. The best results were obtained with the 475 nm and 605 nm wavelengths with algae and cyanobacteria, respectively. In order to obtain a higher sensitivity to measure the photosynthetic response to bioactive molecules, the intensity of the low excitation light was adjusted in order to obtain a $F_1$ fluorescence level a little higher than $F_0$.

Fluorescence measured 2 seconds after tuning on one LED is $F_1$ (current applied to the LED to produce a variation in the light intensity between 0 and 1.6 mV). Three additional LEDs are then turned on so as to induce actinic illumination $F_2$ (current applied to LEDs to produce a variation in the light intensity between 2 and 20 mV). Light beams are oriented so as to form together a point of convergence precisely at the level where the photodiode is read. After a specific time, chosen according to the nature of the algal species used, of the background noise and of the level of sensitivity sought, the $F_2$ fluorescence is measured. To determine $F_1$ and $F_2$, the fluorometer measures wavelengths higher than 700 nm. The gain (signal integration varying as selected from 0.32 to 80 msec) and the delay (the delay of 0, 1 to 1000 msec required by LEDS in order to produce the actinic illumination after photosystems activation) are adjusted to obtain optimal sensitivity, $F_1$ and $F_2$ readings.

The photosynthetic efficiency is determined with the following formula $(F_2-F_1)/F_2$. Any molecule affecting directly or indirectly the photosystems modify either $F_1$ or $F_2$ which modification necessarily decreases the photosynthetic efficiency. The inhibition curve of a particular molecule is determined by calculating the activity of the photosystems in the absence of the molecule and in the presence of the molecule and comparing both efficiency as follows as described in Conrad 1993:

Without Inhibitor (wi):

$$\text{efficiency}_{(wi)}=(F_{2(wi)}-F_{1(wi)}/F_{2(wi)}$$

With Inhibitor:

$$\text{Relative photosynthetic efficiency}_{(sample)}=(F_{2(sample)}-F_{1(sample)})/F_{2(wi)}$$

Percentage Efficiency:

$$\text{efficiency (\%)}=(\text{efficiency}_{(sample)}\times 100)/\text{efficiency}_{(wi)}$$

Percentage Inhibition:

$$\text{Inhibition (\%)}=100-\text{efficiency (\%)}$$

The present invention is illustrated in further detail by the following non-limiting examples.

EXAMPLE 1

Preparation of *Chlorella vulgaris*

The *Chlorella vulgaris* were obtained from UTCC (University of Toronto Culture Collection) or UTEX (The Culture Collection of Algae at the University of Texas at Austin). They were cultivated under an illumination of at most 3500 lux (fluorescent lamps) and at a temperature of 28° C. with a periodicity of about 16 hours of illumination followed by 8 hours of darkness in a sterilized culture medium BBM (Bold Basal Freshwater Nutrient Solution).

Stabilization of *Chlorella vulgaris*

When the *Chlorella* reached exponential growth phase (i.e. namely between 7 and 15 days) (depending on the initial concentration and/or the physiological state of the inoculum), they were concentrated either by centrifugation (1575×g) or by gravity for 24 hours at 4° C. The supernatant was replaced by fresh supernatant. The *Chlorella* were stored at 4° C. in amber bottles of 5 mL. It is useful to allow the microorganisms used in the present invention to reach their exponential growth phase because it is generally at that phase that they reach optimal photosynthetic activity.

Just before testing, the *Chlorella vulgaris* were reactivated by exposing them to ambient light and room temperature for 90 minutes. This reactivation promoted optimal photosynthetic activity.

A hundred μL or 50 μL of *Chlorella vulgaris* were used with 2 mL of aqueous solution (i.e. distilled water) to test. 100 μL and 50 μL of *Chlorella vulgaris* correspond to $5\times10^6$ and $2.5\times10^6$ cells/mL, respectively.

EXAMPLE 2

Preparation of *Dunaliella Tertiolecta*

The *Dunaliella tertiolecta* were obtained from UTCC (University of Toronto Culture Collection) or UTEX (The Culture Collection of Algae at the University of Texas at Austin). They were cultivated under an illumination of at most 3500 lux (fluorescent lamps) and at room temperature with a periodicity of about 12 hours of illumination followed by 12 hours of darkness in a culture medium f/2 (Sigma, UTEX) produced with sterilized sea water. *Dunaliella tertiolecta* were used when they were in their exponential growth phase.

*Dunaliella tertiolecta* were retrieved from their culture medium 45 minutes after the beginning of the illumination period. This reactivation promoted optimal photosynthetic activity. 500 μL of the algae were used in 2 mL of aqueous solution (i.e. distilled water). 500 μL of *Dunaliella tertiolecta* corresponds to 200 000 to 350 000 cells/mL.

EXAMPLE 3

Preparation of *Anabaena* sp.

The *Anabaena* sp. were obtained from UTCC (University of Toronto Culture Collection) or UTEX (The Culture Collection of Algae at the University of Texas at Austin). They were cultivated under an illumination of at most 1000 lux (originating from fluorescent lamps) and at room temperature with a periodicity of about 16 hours of illumination followed by 8 hours of darkness in a sterilized culture medium BG11 (University of Toronto). *Anabaena* sp. were used when they were in their exponential growth phase.

*Anabaena* sp. were retrieved from their culture medium 60 minutes after the beginning of the illumination period. This reactivation promoted optimal photosynthetic activity. 100 μL of the algae were used in 2 mL of aqueous solution (i.e. distilled water) to test. This 100 μL of *Anabaena* sp. corresponds to $1\times10^7$ cells/m L.

EXAMPLE 4

Assessing stability of *Chlorella vulgaris*

The stability of *Chlorella vulgaris* was evaluated by determining the $Cl_{20}$ of atrazine using seven different atrazine concentrations. $Cl_{20}$ is the concentration of atrazine inhibiting 20% of the efficacy emitted by *Chlorella vulgaris* as compared to a control *Chlorella vulgaris* preparation. The $Cl_{20}$ is statistically determined with the software Icp version 2.0. Stability over time is determined by assessing the number of $Cl_{20}$ within a range of 2 σ of average.

A *Chlorella vulgaris* culture was prepared as described in Example 1 above. As indicated above, the algae were reactivated before testing during 90 minutes under ambient light and at room temperature.

The culture was then incubated with atrazine for 10 minutes under green light and at room temperature. The cellular concentration of the algae was $5\times10^6$ cells/mL of solution (100 μL algae in 2 mL of atrazine-containing aqueous solution (i.e. distilled water)). The concentration of atrazine varied between 0 and 0.04 mg/L. Testing was performed in triplicates. The fluorescence emitted by each formulation was then measured with Luminotox™, a fluorometer that measures photosynthetic activity.

Figure 2:
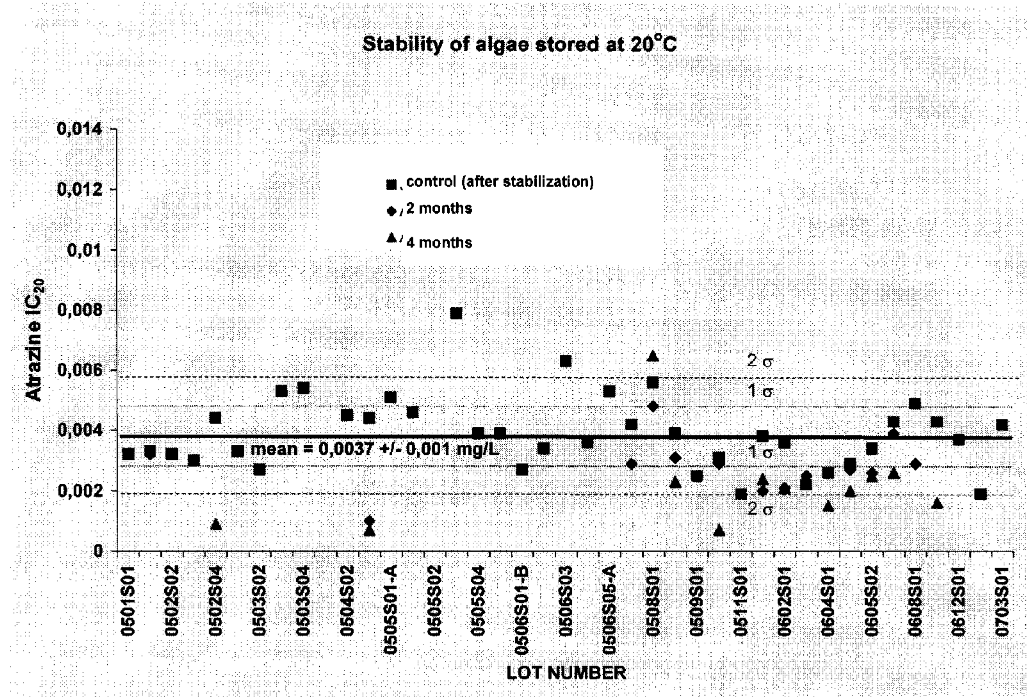
FIG. 2 demonstrates the stability of *Chlorella vulgaris* at 20° C.

FIGS. 1 and 2 show that *chlorella vulgaris* stored at 4° C. are stable for at least 6 months and at 20° C. are stable at least four months. $Cl_{20}$ is contained within average (0.0037)+ or − two a (namely 0.002).

EXAMPLE 5

Effect of pH on the Detection of Bioactive Molecules

A *Chlorella vulgaris* culture was prepared as described in Example 1 above. As indicated above, the algae were reactivated before testing during 90 minutes under ambient light and at room temperature.

The culture was then incubated with ammoniacal nitrogen for 10 minutes under green light and at room temperature. The desired pH was achieved by adding NaOH to a glycine 20 mM buffer. The cellular concentration of the algae was $5\times10^6$ cells/mL of solution (100 μL algae in 2 mL of ammoniacal nitrogen containing aqueous solution (i.e. distilled water)). Testing was performed in triplicates. The fluorescence emitted by each formulation was then measured with Luminotox™, a fluorometer that measures photosynthetic activity. Although the Luminotox™ was used in Examples presented herein, any fluorometer able to measure synthetic activity can be used in accordance with the present invention.

Figure 3:
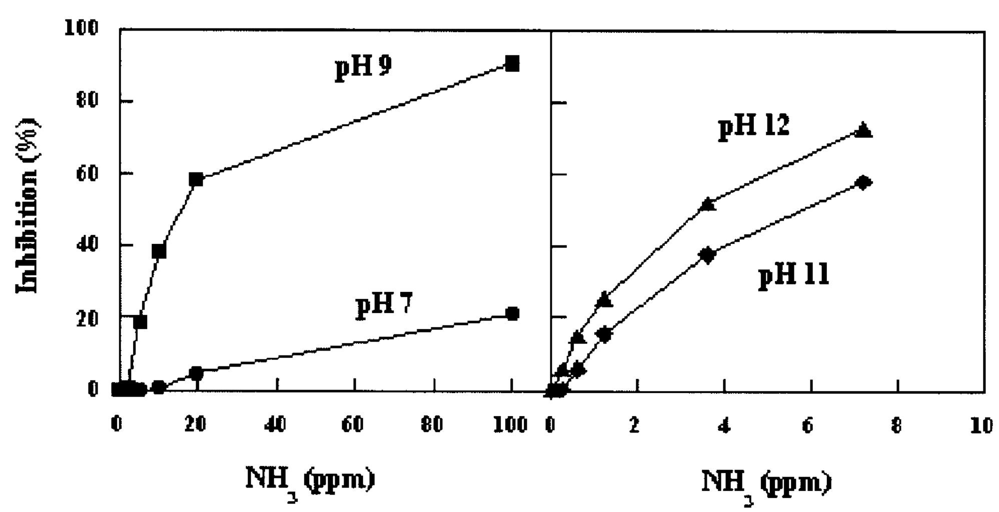
FIG. 3 demonstrates the effect of pH on the inhibition of *Chlorella Vulgaris* during the detection of ammonia nitrogen.

FIG. 3 shows that as the pH was raised from 7 to 12, the percentage inhibition of *Chlorella vulgaris* was increased. Indeed, at pH=7, a 20% inhibition was achieved when the concentration of $NH_3$ was 100 ppm whereas at pH=9, a 20% inhibition was achieved when the concentration of $NH_3$ was only 5 ppm. When the pH had a value of 11 or 12, the 20% inhibition was achieved when the concentration of $NH_3$ was lower than 2 ppm. Thus, a basic pH allowed a better detection of ammoniacal nitrogen. Since the difference in testing sensibility between a pH of 11 and a pH of 12 was rather small, a pH of 11 is preferred since the algae better tolerates this pH.

EXAMPLE 6

Effect of Temperature on the Detection Of bioactive Molecules

A *Chlorella vulgaris* culture was prepared as described in Example 1 above. As indicated in Example 1, the algae were reactivated before testing under ambient light and at room temperature during 90 minutes.

The culture was then incubated for 10 minutes with atrazine at increasing concentrations under green light at neutral pH, and at temperatures of 20, 25, 30, 35 or 40° C. The cellular concentration of the algae was $5\times10^6$ cells/mL (100 μL algae in 2 mL of atrazine containing aqueous solution (i.e. distilled water)). The temperature was controlled with a thermostatic bath. Testing was performed in triplicates. The fluorescence emitted by each formulation was then measured with Luminotox™, a fluorometer that measures photosynthetic activity.

Figure 4:
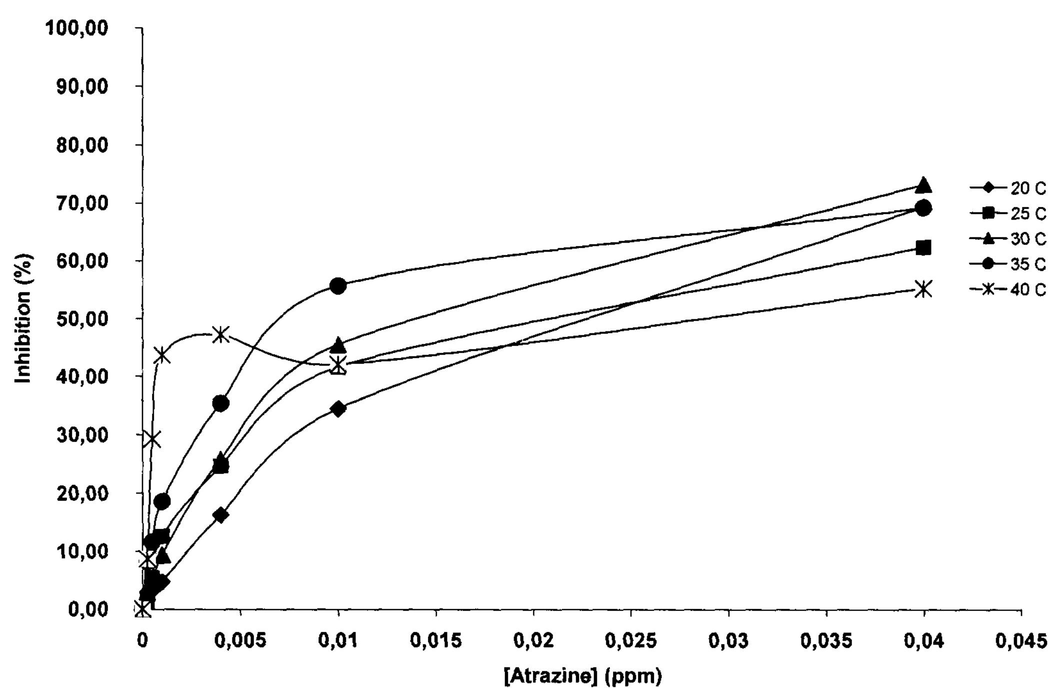
FIG. 4 demonstrates the effect of temperature on the inhibition of *Chlorella Vulgaris* during the detection of atrazine.

FIG. 4 shows that for concentrations of atrazine lower than 0.005 ppm, the percentage of inhibition increases as the temperature increases. For low concentrations, an increase in temperature enhances the limit of detection of atrazine. FIG. 2 also shows that for concentrations of atrazine higher than 0.01 ppm, testing sensibility decreased at 40° C. The optimum temperature for both high and low concentrations was thus observed to be 35° C. for *Chlorella vulgaris.*

Without being bound by theory, it is submitted that pH and temperature have a significant influence on the inhibition of the photosynthetic activity of the algae because they modulate the diffusion of bioactive molecules through the lipid bilayer of the plant cells. pH is especially important when the bioactive molecule is an ion because ions have more difficulty penetrating the lipid bilayer due to their charge. Furthermore, subjecting algae to temperatures higher than those necessary for algae growth results in an increase of inhibition of the photosynthetic activity of the plant as well as an increase of the permeability of the lipid bilayer. Increasing the membrane permeability leads to an increase of toxic molecules within the cells which results in an enhanced inhibition of these cells and higher fluorescence readings.

EXAMPLE 7

Effect of Light Exposure of Algae Combined with a Low Concentration of Algae and Increased Temperature on the Detection of Bioactive Molecules A *Chlorella vulgaris* culture was prepared as described in Example 1 above. As indicated in Example 1, the algae were reactivated before testing under ambient light and at room temperature during 90 minutes.

The culture was then incubated with various concentrations of copper or cyanides. Testing with cyanides was performed for 15 minutes at 35° C. under ambient light and under green light at room temperature. Testing with copper was performed at 35° C. under ambient light for 15 and 60 minutes and under green light at room temperature for 60 minutes. The cellular concentration of the algae was $2.5\times10^6$ cells/mL (50 μL of algae in 2 mL copper or cyanides containing aqueous solution (i.e. distilled water)). Testing was performed in triplicates. The fluorescence emitted by each formulation was then measured with Luminotox™, a fluorometer that measures photosynthetic activity.

Figure 5:
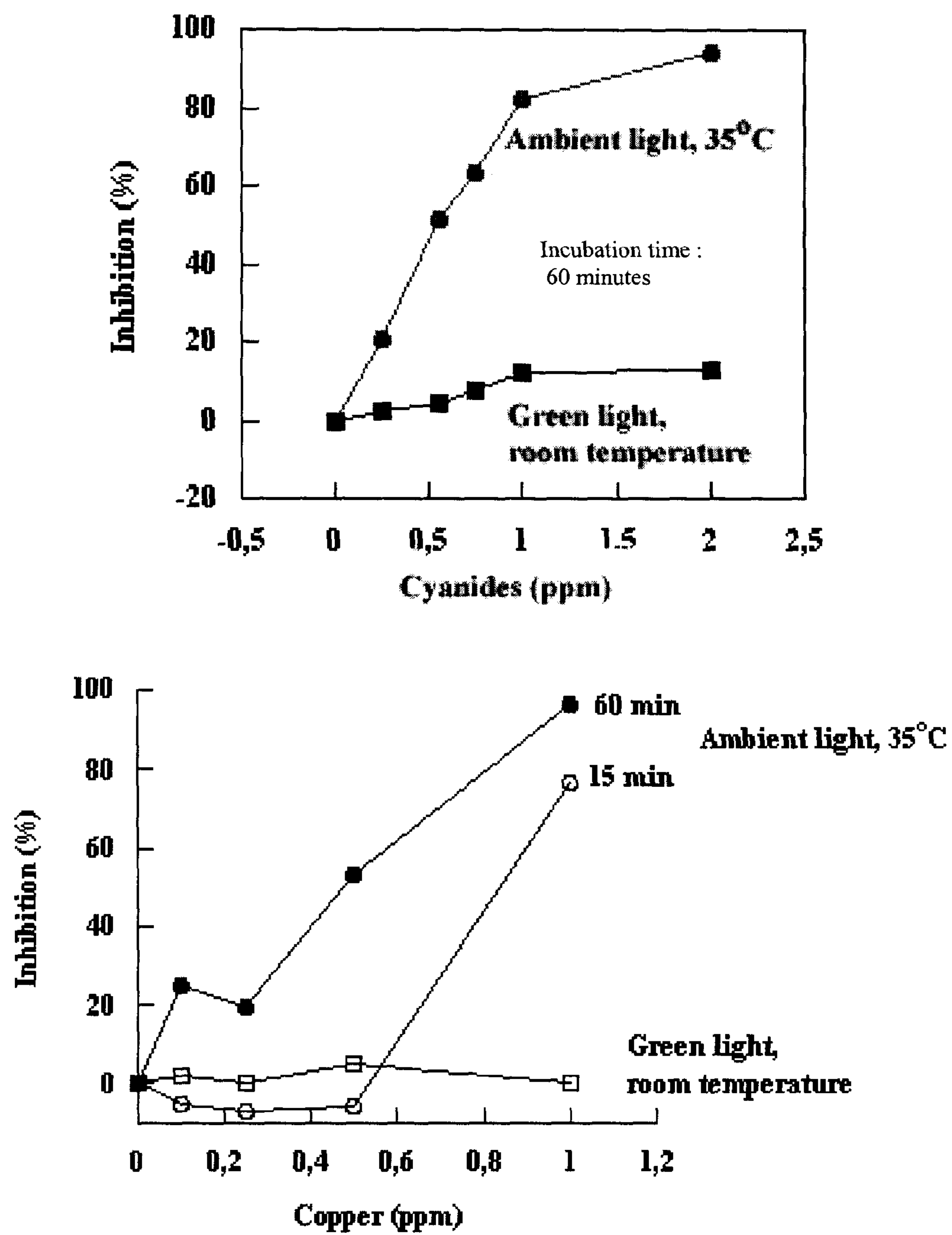
FIG. 5 demonstrates the effect of exposing *Chlorella Vulgaris* to white light during the detection of cyanides and copper.

FIG. 5 shows that for both bioactive molecules, the percentage inhibition is greater when testing is done under ambient light at a temperature of 35° C. than when testing is done under green light at room temperature.

Without being bound by theory, it is submitted that exposing algal cells to light having an intensity higher than required for photosynthesis saturation results in an increased inhibition of photosynthesis and thus allows for enhanced inhibition of these cells and results in higher fluorescence readings thus enhancing the detection of bioactive molecules.

EXAMPLE 8

Comparison of Exposure to White Light Followed by Recovery Under Green Light with Exposure to Green Light Only A *Dunaliella tertiolecta* culture was prepared as described in Example 2 above. As indicated in Example 2, the algae were reactivated before testing under ambient light and at room temperature during 45 minutes.

The formulation was then incubated with progesterone at concentrations of 0; 0.05; 0; 5 or 1 ppm for 15 minutes under green light only or for 15 minutes under ambient light followed by 5 to 35 minutes under green light. The cellular concentration was 350 000 cells/mL (500 μL of algae within 2 mL of progesterone containing aqueous solution (i.e. distilled water)). Testing was performed in triplicates. The fluorescence emitted by each formulation was then measured with Luminotox™, a fluorometer that measures photosynthetic activity.

Figure 6:
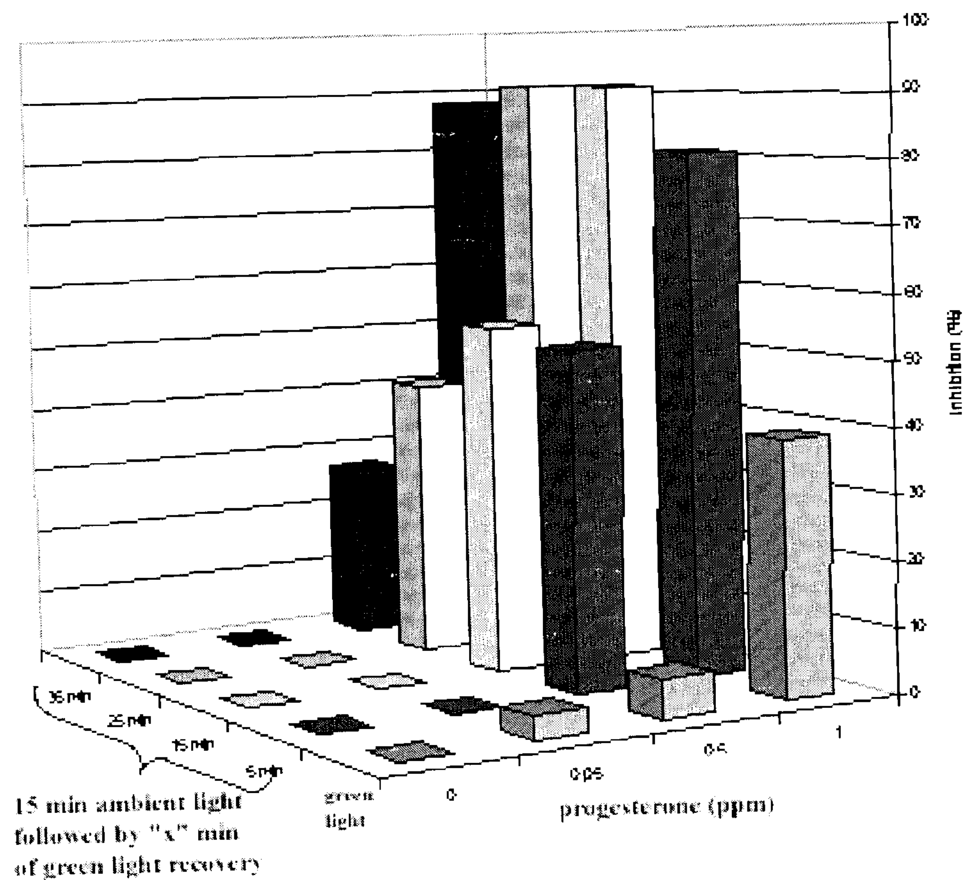
FIG. 6 demonstrates the effect of exposing *Dunaliella Tertiolecta* to white light and subsequently to green light during the detection of progesterone.

FIG. 6 shows that when the algae is exposed to green light only in the presence of progesterone, the maximum percentage inhibition obtained is 40% when the progesterone concentration is 1 ppm. Substantially higher percentage inhibitions were obtained when the algae was exposed to white light for 15 minutes followed by a recovery in green light.

It is well known in the art that photosynthesis does not occur under green light nor does it occur in the dark. Thus, substituting the recovery in green light with a recovery in the dark is expected to yield results similar to those shown in FIG. 6.

EXAMPLE 9

Comparison of Exposure to White Light Followed by Recovery Under Green Light with Exposure to White Light Only An *Anabaena* sp. culture was prepared as described in Example 3 above. As indicated in Example 3, the cyanobacteria were reactivated before testing under ambient light and at room temperature during 60 minutes.

The culture was then incubated with bioactive molecules listed in Table 1 below at concentrations of 1 ppm (except for atrazine which was used at a concentration of 1 ppb) for 10 minutes under ambient light followed by 10 minutes under green light and neutral pH. The cellular concentration was $1.0\times10^7$ cells/mL (100 μL of cyanobacteria within 2 mL of bioactive agent containing aqueous solution (i.e. distilled water)). Testing was performed in triplicates. The fluorescence emitted by each formulation was then measured with Luminotox™ a fluorometer that measures photosynthetic activity.

TABLE 1

Results of detection of various bioactive molecules with *Anabaena*

| | Inhibition obtained at 1 ppm (10 min ambiant light) → % | Inhibition obtained at 1 ppm (followed by 10 min green light) % |
|---|---|---|
| aldicarbe | 0 | 30 |
| atrazine (1 ppb) | 1 | 13 |
| bentazone | 0 | 28 |
| chlorpyrifos | 0 | 10 |
| cyanure | 0 | 16 |
| dicrotophos | 2 | 17 |
| glyphosate | 0 | 7 |
| gramicidine | 0 | 15 |
| malathion | 0 | 17 |
| metolachlor | 0 | 22 |
| tetracycline | 0 | 30 |

Table 1 shows that exposition of *Anabaena* to ambient light only in the presence of the various bioactive molecules did not produce a detectable inhibition at the specified concentration of bioactive molecules. The cyanobacteria were thus advantageously then exposed to green light to induce a detectable inhibition.

EXAMPLE 10

Effect of the Ambient Light, Temperature and Low Algae Concentration on Cyanide and Copper Detection A *Chlorella vulgaris* culture was prepared as described in Example 1 above. As indicated in Example 1, the algae were reactivated before testing under ambient light and at room temperature during 90 minutes.

The algae formulation was then incubated for 15 or 60 minutes with water containing copper or cyanides at the indicated concentrations (FIG. 7) under ambient light at a temperature of 35° C. and at a neutral pH. Algae concentrations of $2.5\times10^6$ cells/mL and $5\times10^6$ cells/mL (50 μL and 100 μL of algae, respectively within 2 mL of metal containing aqueous solutions (i.e. distilled water)) were tested. Testing was performed in triplicates. The fluorescence emitted by each formulation was then measured with Luminotox™, a fluorometer that measures photosynthetic activity.

Figure 7:
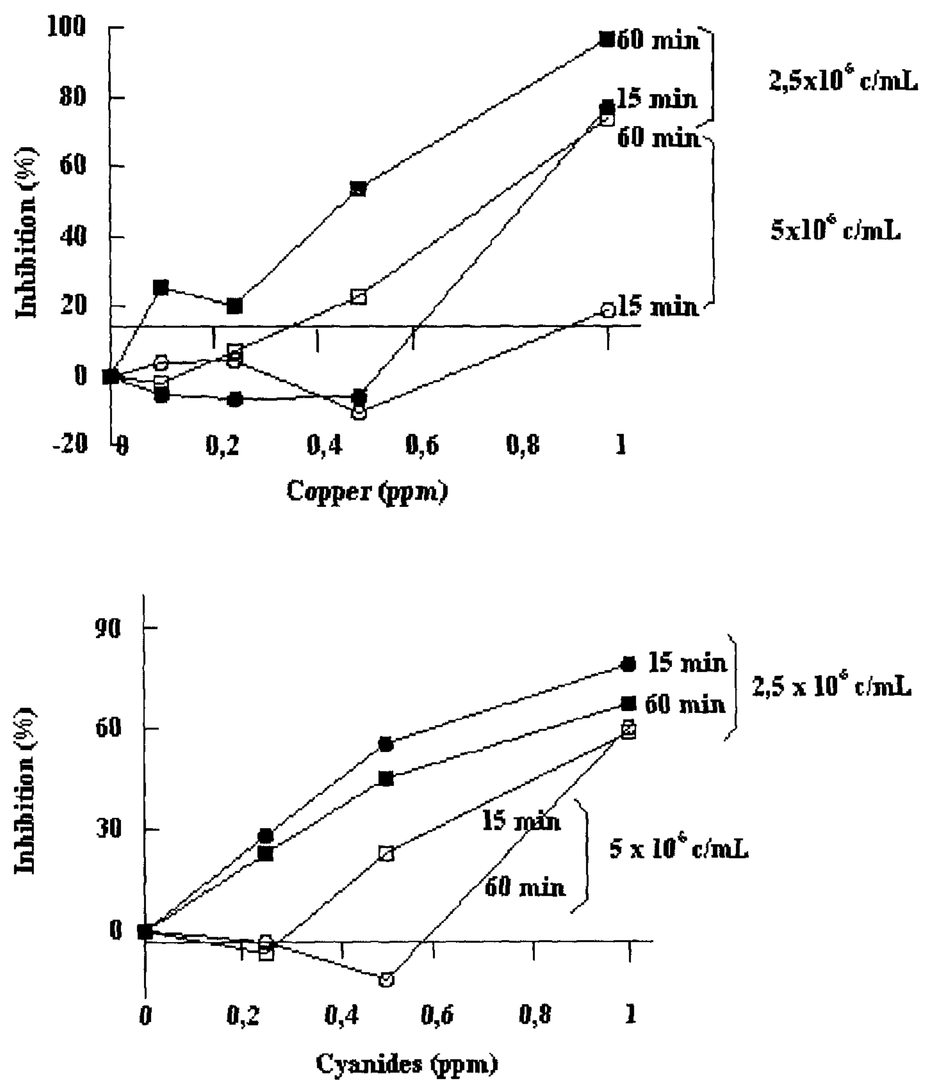
FIG. 7 demonstrates the effect of using a low cellular concentration of *Chlorella vulgaris* during the detection of copper and cyanides.

FIG. 7 shows the effect of the initial cellular concentration of the algae, temperature and ambient light when detecting cyanides and copper. The use of the lower cellular concentration yields higher percentage inhibitions of the algae and thus a better limit of detection of bioactive molecules.

EXAMPLE 11

Figure 8:
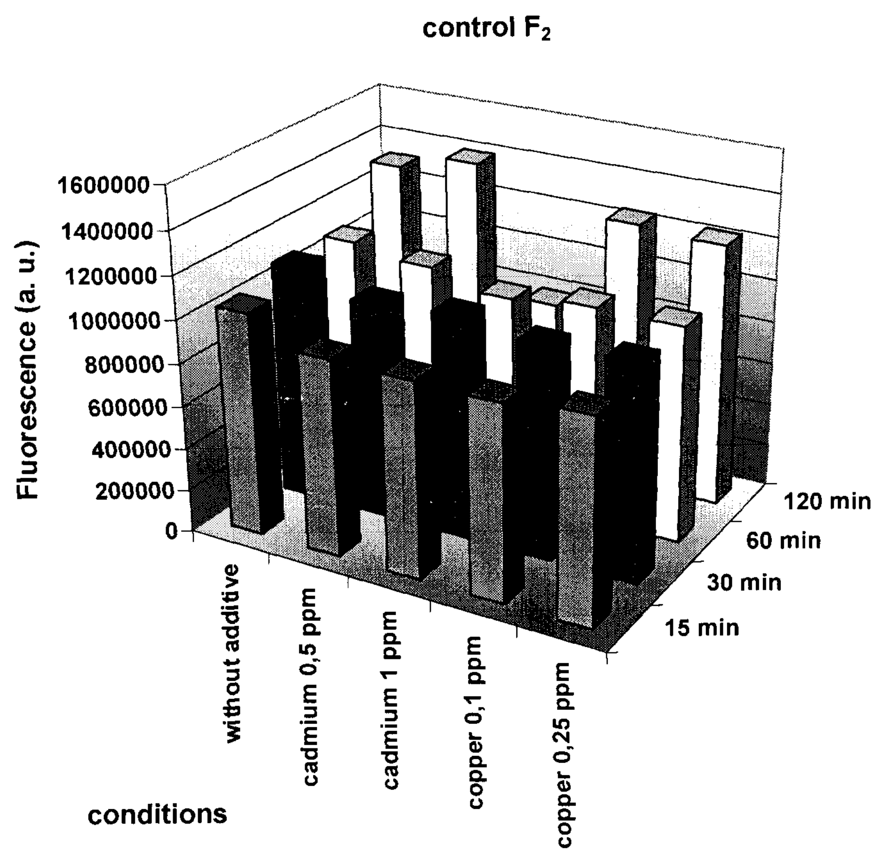
FIG. 8 shows the effect of various concentrations of cadmium and copper on $F_2$ fluorescence over time.

Stability of $F_2$ Fluorescence after up to 120 Minutes of Incubation $F_2$ fluorescence levels produced by *Chlorella vulgaris* prepared as described in Example 1 above was measured after incubation with additives tested above, namely cadmium (0.5 ppm), cadmium (1 ppm), copper (0.1 ppm) and copper (0.25 ppm). As may be seen in FIG. 8, $F_2$ fluorescence was stable after up to 120 minutes of incubation for each of these additives. Only cadmium at 1 ppm induced a decrease of fluorescence after 120 minutes of incubation so that it may be desirable to use Cd as additive at a concentration lower than 1 ppm.

EXAMPLE 12

Effect of Time of Incubation, Ambient Light, Temperature, Additive and Low Algae Concentration on the Detection of Bioactive Molecules A *Chlorella vulgaris* culture was prepared as described in Example 1 above. As indicated in Example 1, the algae were reactivated before testing under ambient light and at room temperature during 90 minutes.

The formulation was then incubated under ambient light at 35° C. and at neutral pH with cadmium, copper, chromium, zinc, nickel, or lead, at indicated concentrations at incubation times varying between 15 minutes and 120 minutes. (FIGS. 9 to 12). The formulations were tested without additives or with 1 ppm cadmium, 0.1 ppm copper or 0.25 ppm copper as additive. The cellular concentration was $2.5\times10^6$ cells/mL (50 μL of algae within 2 mL of metal containing aqueous solution (i.e. distilled water)). Testing was performed in triplicates. The fluorescence emitted by each formulation was then measured with Luminotox™, a fluorometer that measures photosynthetic activity.

Figure 9:
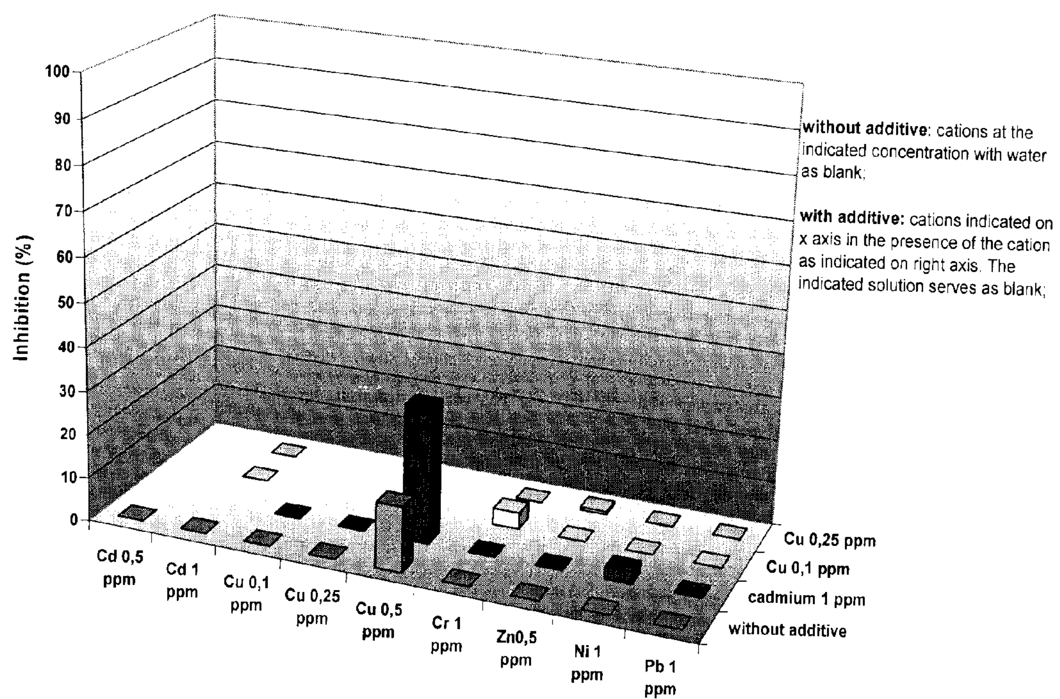
FIG. 9 compares the effect of copper or cadmium as additives during the incubation step for an incubation time of 15 minutes for the detection of a plurality of metals at various concentrations using *Chlorella vulgaris*. For calculating the inhibition provided by a metal-containing sample with additive, the corresponding additive solution served as control whereas for calculating the inhibition produced by the metal containing sample without additive, the water sample served as control (blank)
Figure 10:
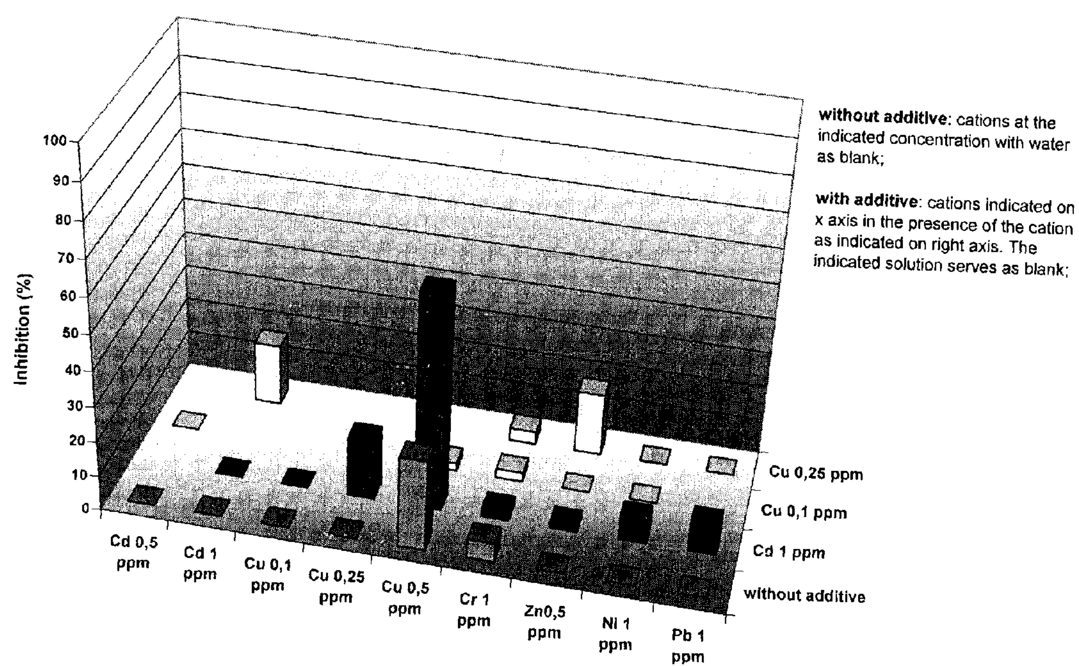
FIG. 10 demonstrates the effect of the use of copper or cadmium as additives during the incubation step at white light and 35° C. for an incubation time of 30 minutes for the detection of a plurality of metals at various concentrations using *Chlorella vulgaris*. The control and blank used are as described in FIG. 9.
Figure 11:
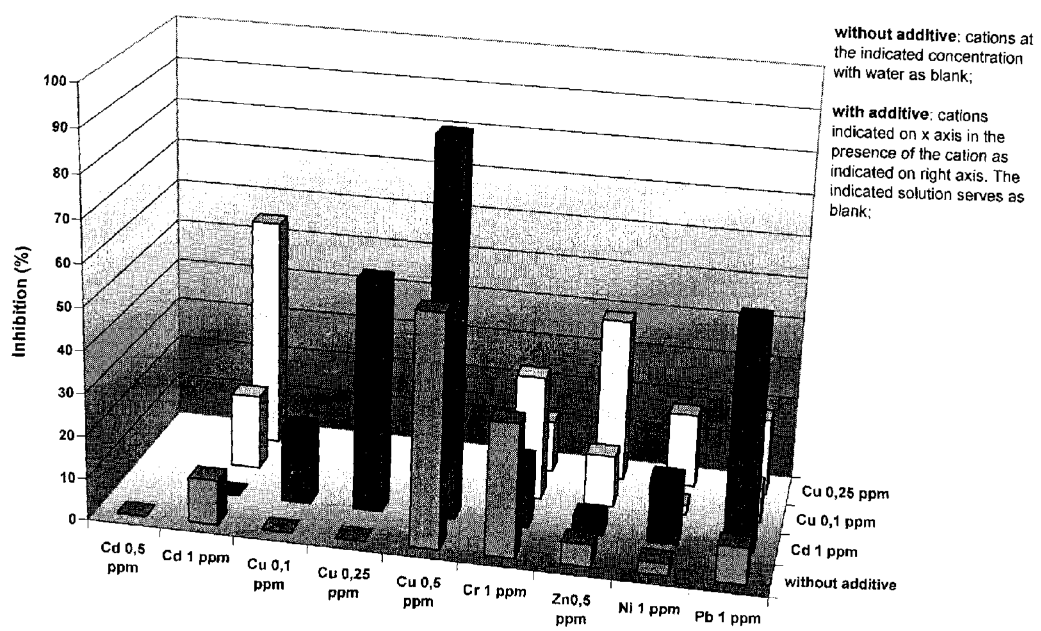
FIG. 11 demonstrates the effect of the use of copper or cadmium as additives during the incubation step for an incubation time of 60 minutes for the detection of a plurality of metals using *Chlorella vulgaris*. The control and blank used are as described in FIG. 9.
Figure 12:
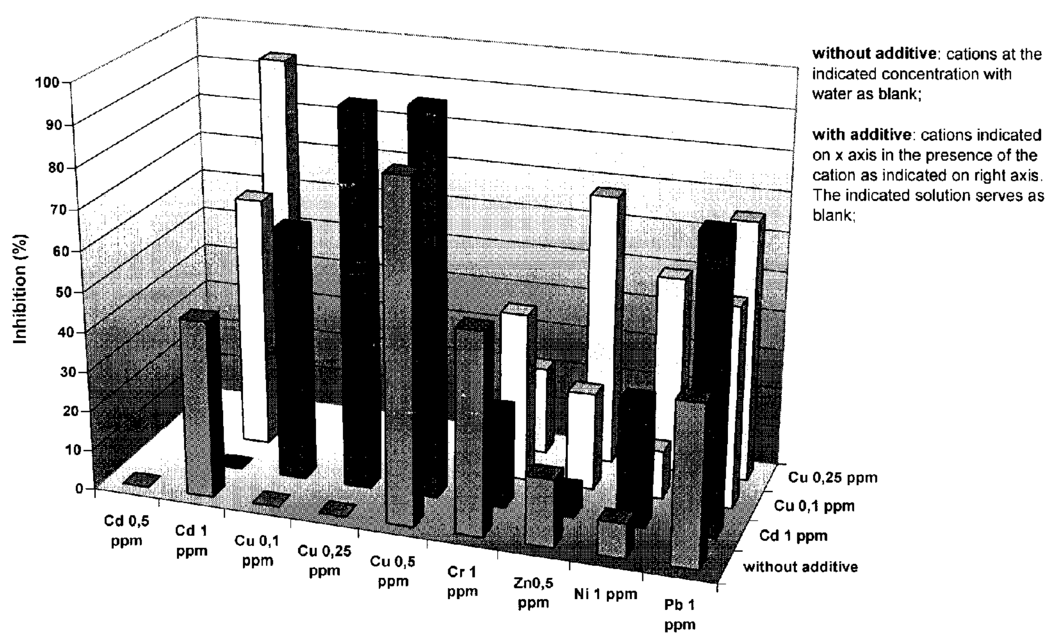
FIG. 12 demonstrates the effect of the use of copper or cadmium as additives during the incubation step for an incubation time of 120 minutes for the detection of a plurality of metals using *Chlorella vulgaris*. The control and blank used are as described in FIG. 9.

FIG. 9 shows that after 15 minutes of incubation, only copper at 0.5 ppm was detected (15% inhibition) without additive and that the addition of cadmium at a concentration of 1 ppm increased the inhibition to 30%. Cadmium at 1 ppm alone was not detected. After 30 minutes of incubation (FIG. 10), cadmium 1 ppm and zinc 0.5 ppm were detected in the presence of copper 0.25 ppm and produced a fluorescence inhibition above 10%. The detection of copper increased with incubation time.

After 60 minutes of incubation (FIG. 11), without additive, cadmium 1 ppm, chromium 0.1 ppm and lead 1 ppm were detected although weakly. The addition of 1 ppm lead increased the percentage of inhibition of copper 1 ppm, nickel 1 ppm and copper 0.1 ppm and 0.25 ppm. Chromium is better detected alone or in the presence of copper 0.1 ppm than in the presence of cadmium 1 ppm (antagonistic effect) or copper 0.25 ppm. Copper at a concentration of 0.25 ppm increases the detection of cadmium 1 ppm, zinc 0.5 ppm and nickel 1 ppm. Copper 0.25 ppm is not detected without additives.

After 120 minutes of incubation (FIG. 12), nickel 1 ppm is weakly detected. The addition of copper at 0.25 ppm increases the detection of cadmium (1 ppm), zinc (0.5 ppm)

and nickel (1 ppm). Adding cadmium 1 ppm increases the detection of lead (1 ppm) and copper (0.5 ppm).

EXAMPLE 13

Effect of Time of Incubation, Ambient Light, Temperature, Additive and Low Algae Concentration on the Detection of Lead A *Chlorella vulgaris* culture was prepared as described in Example 1 above. As indicated in Example 1, the algae were reactivated before testing under ambient light and at room temperature during 90 minutes.

The formulation was then incubated under ambient light at 35° C. and at neutral pH with lead, at indicated concentrations and at incubation times varying between 15 minutes and 120 minutes (FIGS. 13 to 16). The formulations were tested with or without additives used as single additives (Cd 1 ppm, Cu 0.1 ppm and Cu 0.25 ppm) or mixes of additives (Cu 0.1 ppm+Cd 0.5 ppm; Cu 0.1 ppm+Cd 1 ppm; Cu 0.25 ppm+Cd 1 ppm). The cellular concentration was $2.5\times10^6$ cells/mL (50 μL of algae within 2 mL of lead containing aqueous solution (i.e. distilled water) with or without additives). Testing was performed in triplicates. The fluorescence emitted by each formulation was then measured with Luminotox™ a fluorometer that measures photosynthetic activity.

Figure 13:
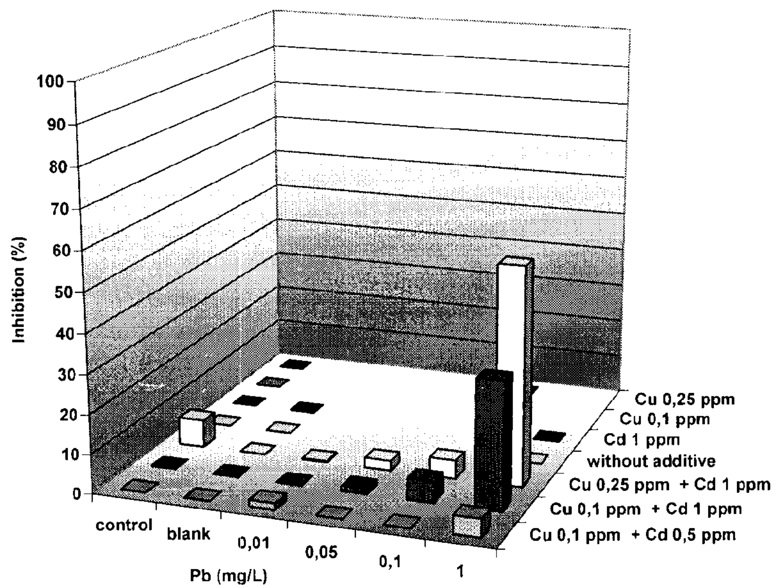
FIG. 13 demonstrates the effect of various single additives or mixtures of additives with an incubation time of 15 minutes for the detection of lead using *Chlorella vulgaris*. For calculating the inhibition provided by a lead-containing sample with additive, the corresponding additive solution without lead served as control (control) whereas for calculating the inhibition produced by the lead-containing sample without additive, the water sample served as control (blank)
Figure 14:
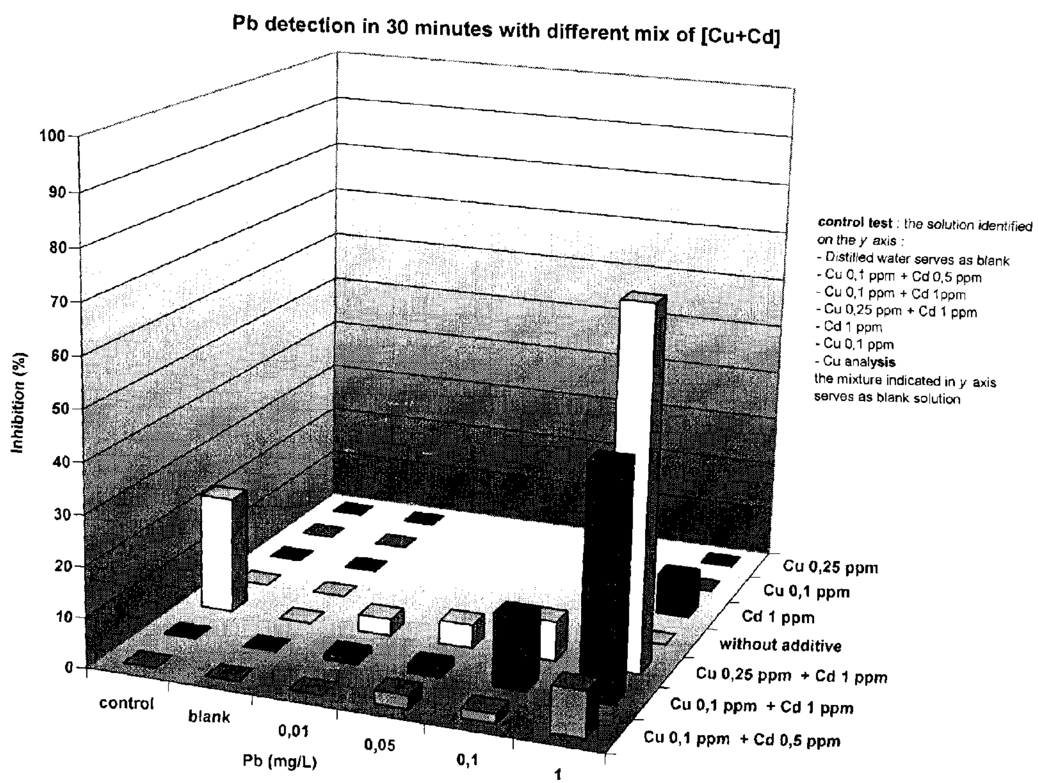
FIG. 14 demonstrates the effect of various single additives or mixtures of additives with an incubation time of 30 minutes for the detection of lead using *Chlorella vulgaris*. The control and blank used are as described in FIG. 13.
Figure 15:
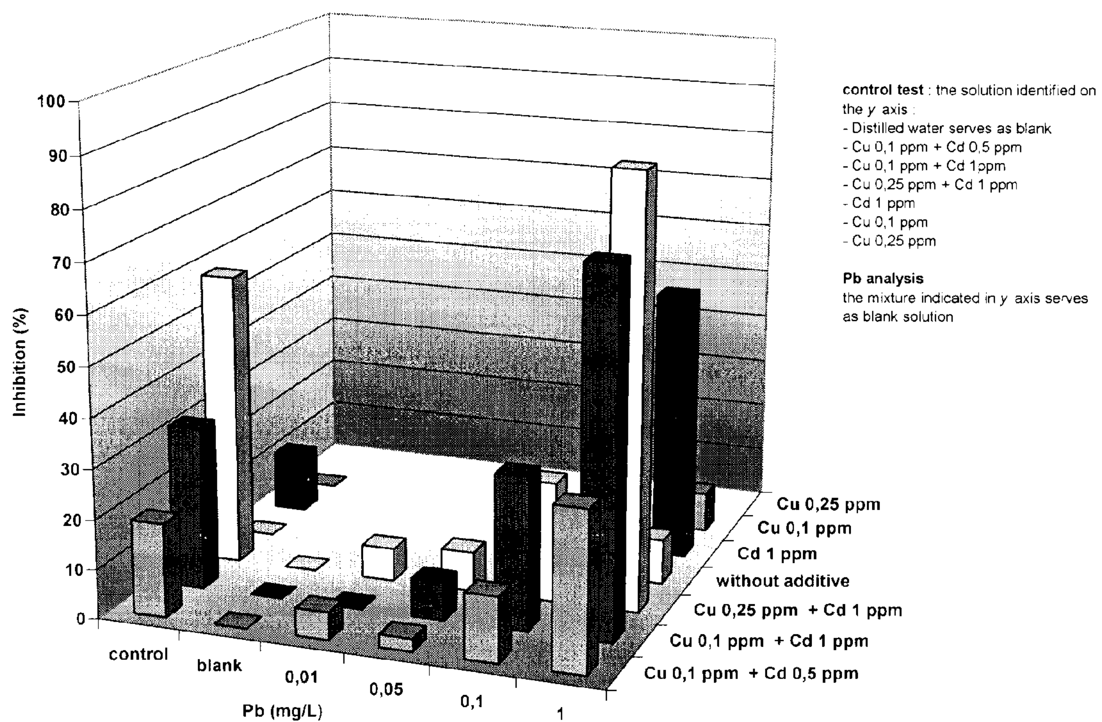
FIG. 15 demonstrates the effect of various single additives or mixtures of additives with an incubation time of 60 minutes for the detection of lead using *Chlorella vulgaris*. The control and blank used are as described in FIG. 13.
Figure 16:
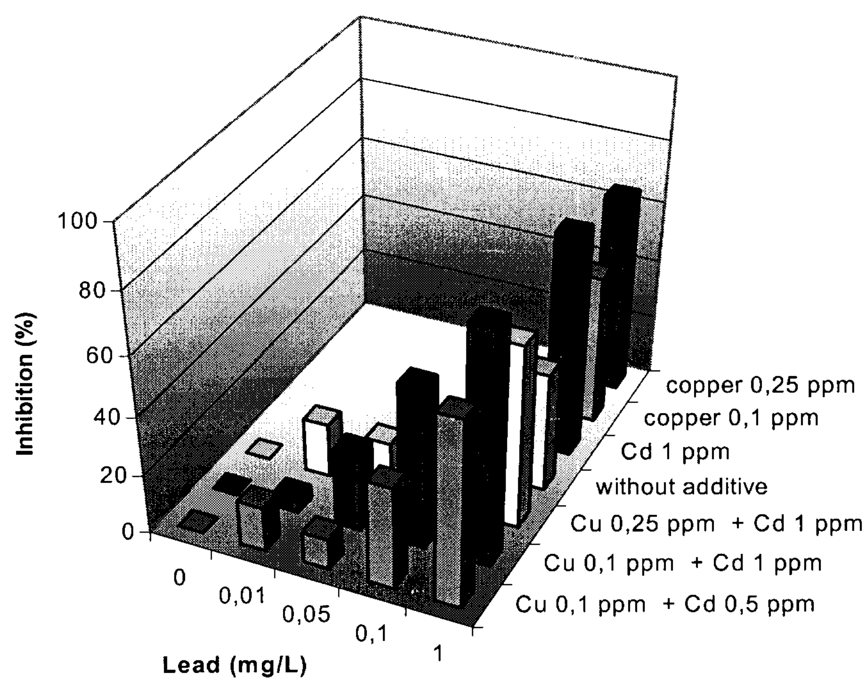
FIG. 16 demonstrates the effect of various single additives or mixtures of additives with an incubation time of 120 minutes for the detection of lead using *Chlorella vulgaris*. The control and blank used are as described in FIG. 13.

FIG. 13 shows that after 15 minutes of incubation, only lead (1 ppm) was detected with mixtures of additives After 30 minutes of incubation (FIG. 14), lead was detected at 0.1 ppm with the mixture Cu 0.1 ppm+Cd 1 ppm.

After 60 minutes of incubation (FIG. 15), all additive mixtures increased the detection of lead at a concentration of 0.1 ppm or more.

After 120 minutes of incubation (FIG. 16), lead was detected at 0.01 ppm (2007 Canadian norm for drinkable water) with additive mixtures Cu 0.1 ppm+Cd 0.5 ppm and Cu 0.25 ppm+Cd 1 ppm. However, the additive mixture that least affects the initial fluorescence as compared to the aqueous solution (i.e. distilled water) is Cu 0.1 ppm+Cd 0.5 ppm. The latter thus represent the best choice for the detection of lead.

It is reasonably predictable that several other additives and additive mixtures could be used for the purpose of increasing inhibition of contaminants. Chlorpyriphos for the detection of atrazine (Lydy and Linck, 2003), phenylureas for the detection of other phenylureas (Detection et al., 2004b); triazines for the detection of other triazines (Faust et al., 2001), copper, nickel or chromium for the detection or other contaminants (Rai et al.), copper for organic contaminants such as polycyclic aromatic hydrocarbons (Babu et al., 1001 and 2005), and strong oxidizing agents such as $H_2O_2$ for the detection of cyanides and other inorganic compounds and substances.

EXAMPLE 14

Effect of the Ambient Light, Temperature and Low Algae Concentration on Tetracycline Detection A *Chlorella vulgaris* culture was prepared as described in Example 1 above. As indicated in Example 1, the algae were reactivated before testing under ambient light and at room temperature during 90 minutes.

The algae formulation was then incubated for 15 or 60 minutes with water containing tetracycline at the indicated concentrations (FIG. 17) under ambient light at a temperature of 35° C. and at a neutral pH. Algae concentrations of $2.5\times10^6$ cells/mL (50 μL of algae within 2 mL of tetracycline-containing aqueous solutions (i.e. distilled water)) were tested. Testing was performed in triplicates. The fluorescence emitted by each formulation was then measured with Luminotox™, a fluorometer that measures photosynthetic activity.

Figure 17:
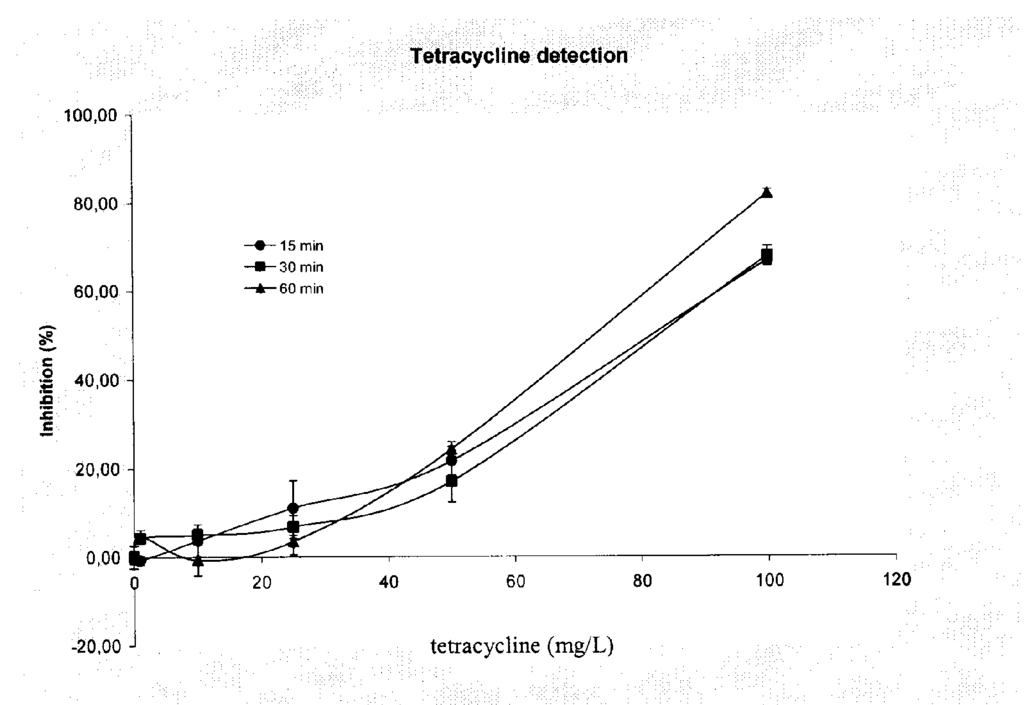
FIG. 17 demonstrates the effect of using ambient light, higher temperature and low cellular concentration of *Chlorella vulgaris* on tetracycline detection.

FIG. 17 shows the effect of the initial cellular concentration of the algae, temperature and ambient light when detecting tetracycline. Tetracycline was detected within 15 minutes at a concentration of 10 μg/mL. Extending the time of incubation did not result in a lower detection threshold.

EXAMPLE 15

Detection Threshold of *Chlorella vulgaris* for Various Bioactive Molecules

A *Chlorella vulgaris* culture was prepared as described in Example 1 above. As indicated in Example 1, the algae were reactivated before testing under ambient light and at room temperature during 90 minutes.

The algae formulations were then incubated for 15 minutes with water containing one of the various contaminants listed in Table 2 below at neutral pH under green light and room temperature or under ambient light at a temperature of 35° C. The algae concentration was $5\times10^6$ cells/mL (100 μL of algae within 2 mL of aqueous solution (i.e. distilled water)) containing the substance to detect at indicated concentrations. For each substances, 5 concentrations in triplicates were tested. The TOXSTAT™ software was used to calculate from inhibition values and standard deviations obtained, the maximum concentration without observable effect and the minimal concentration with observable effects. The threshold was calculated with the following formula: (maximum concentration without observable effect x minimal concentration with observable effects)$^{1/2}$ (See Table 2 below). The temperature was controlled by a thermostatic bath.

The detection threshold was obtained with the geometric mean. It was calculated with the following formula:

$$\text{Detection threshold}=(CSEO\times CMEO)^{1/2}$$ where

CSEO=maximum concentration that does not result in any detectable inhibition on algae efficacy. More specifically, it is the highest tested concentration of which efficacy (inhibition) does not differ from the control.

CMEO=minimal concentration resulting in a detectable inhibition of the algae efficacy. It is the lowest tested concentration of which efficacy significantly differs from that of the control.

CSEO and CMEO were estimated by a variance analysis ANNOVA™ followed by a Dunnett multiple comparison by comparing the mean efficacy of each tested concentration with the control mean. Calculations were performed with TOXSTAT™ (Version 3.5).

EXAMPLE 16

Detection Threshold of *Dunaliella tertiolecta* for Various Bioactive Molecules A *Dunaliella tertiolecta* culture was prepared as described in Example 2 above. As indicated in Example 2, the algae were reactivated before testing under ambient light and at room temperature during 45 minutes.

The algae formulations were then incubated for 15 minutes with water containing one of the various contaminants listed in Table 2 below at neutral pH under green light and at room temperature. The algae concentration was 350 000 cells/mL (500 μL of algae within 2 mL of aqueous solution (i.e. distilled water) containing substance to detect at indicated concentrations). For each substances, 5 concentrations in triplicates were tested. The TOXSTAT™ software was used to calculate from inhibition values and standard deviations obtained, the maximum concentration without observable effect and the minimal concentration with observable effects (See Table 2 below). The temperature was controlled by a thermostatic bath. Tests were performed in triplicates. The fluorescence emitted by each formulation was then measured with Luminotox™, a fluorometer that measures photosynthetic activity and detection threshold determined as described in the Example above.

TABLE 2

| | *Chlorella vulgaris* | | *Dunaliella tertiolecta* |
|---|---|---|---|
| Substances | 10-15 min. green light exposition at room temperature | 10-15 min. exposition to ambiant light at 35° C. | 15 min. green light exposition at room temperature |
| Atrazine | 0.0007 ppm | 0.0.0001 ppm | 0.01 ppm |
| Diuron | <0.0005 ppm | 0.006 ppm | 0.002 ppm |
| Glyphosate | n.d. | 100 ppm | 50 ppm |
| Malathion | n.d. | n.d. | 50 ppm |
| Chlorpyriphos | n.d. | 1 ppm | 1 ppm |
| Dicrotophos | n.d. | n.d. | 235 ppm |
| Cu | n.d. | 0.25 ppm | n.d. |
| Pb | n.d. | <0.5 ppm | n.d. |
| Cd | n.d. | 0.3 ppm | n.d. |
| Hg | n.d. | 0.22 ppm | n.d. |
| Cr | n.d. | n.d. | n.d. |
| Cyanides | n.d. | 0.16 ppm | n.d. |
| Ammonia | 1 ppm at pH 11 | 1 ppm at pH 11 | 1 ppm at pH 11 |
| Nitrogen | n.d. at pH 7 | n.d. at pH 7 | n.d. at pH 7 |

n.d.: not detected.
Concentrations tested for each sample:
Ammonia nitrogen (pH 7): 0; 5; 10; 50; 100; 200
Ammonia nitrogen (pH 11): 0; 0.2; 0.6; 1, 2; 3; 6; 12
Copper (Cu) 0; 0.1; 0.5; 1; 2; 5 ppm
Mercury (Hg): 0.1; 0.5; 1; 2; 5 ppm
Cadmium (Cd): 0; 0.1; 0.5; 1; 2.0; 5.0 ppm
Lead (Pb): 0; 0.1; 0.5; 1; 2.0; 5.0 ppm
Chrome (Cr): 0; 0.1; 0.5; 1; 2.0; 5.0 ppm
Cyanides: 0; 0, 25; 0.5; 1; 5; 10 ppm
Atrazine: 0.00025; 0.0005; 0.001; 0.004; 0.01; 0.04 ppm
Diuron: 0.00025; 0.0005; 0.001; 0.004; 0.01; 0.04 ppm
Glyphosate: 0.01; 0.1; 1.0; 10; 100 ppm
Malathion: 0.01; 0.1; 10; 50 ppm
Chlorpyriphos: 0; 0.01; 0.1; 1 ppm
Dicrotophos: 0.1; 1.0; 10.0; 100; 500 ppm The highest incubation temperature at which inhibition by a bioactive molecule for *Dunaliella tertiolecta* was observed was 30° C.

EXAMPLE 17

Stabilization of Selected Algae for Laboratory and Field Conditions

Algae are stabilized and concentrated by centrifugation to allow a sampling of 100 μL per test (corresponding to a chlorophyll concentration of 10 μg/mL, the commercial test kit contains 50 tests (5 mL). Algae are stored in amber bottles for light protection. They are stable 6 months at 4° C. Their stability is measured with a reference contaminant by measuring its $IC_{50}$ (concentration giving 50% of fluorescence inhibition). The commercial test kits advantageously include more than one microorganism (i.e. monocellular algae or cyanobacteria) for optimal results.

Although the present invention has been described hereinabove by way of specific embodiments thereof, it can be modified, without departing from the spirit and nature of the subject invention as defined in the appended claims.

References

1. François Bellemare, Marie-Eve Rouette, Lucie Lorrain, Élisabeth Perron and Nathalie Boucher (2006). Combined use of photosynthetic enzyme complexes (PECs) and micro-algae photosynthetic systems for rapid screening of wastewater toxicity. *Env. Toxicol.* 21: 445-449

2. Recommandations pour la qualité de'eau potable au Canada, 2007. Comité fédéral-provincial-territorial sur l'eau potable du Comité fédéral-provincial-territorial sur la santé et l'environnement, 15 pages.

The invention claimed is:

1. A method of detecting the presence of bioactive molecules in a fluid sample, comprising activating a microorganism selected from the group consisting of a monocellular algae and a cyanobacteria under ambient light;

contacting a solution of the activated microorganism with the fluid sample so as to obtain a formulation having a microorganism concentration of 200,000-$1\times10^7$ cells/mL of formulation;

incubating the formulation for 10 to 120 minutes at a pH of 7 to 12 and a temperature between 18 and 35° C. under ambient light followed by incubating the formulation for 5 to 120 minutes at a pH of 7 to 12 and a temperature between 18 and 35° C. under green light or darkness; and measuring the fluorescence emitted by the formulation, whereby a fluorescence emitted in the sample that is lower than that in a control sample is an indication that the sample contains a bioactive molecule.

2. The method of claim 1, wherein the incubation under green light or darkness has a duration of about 5 to about 35 minutes.

3. The method of claim 1, wherein the incubation under green light or darkness has a duration of about 15 minutes.

4. The method of claim 3, wherein the incubation pH is between about 11 and 12.

5. The method of claim 4, wherein the monocellular algae is *Chlorella vulgaris*.

6. The method of claim 5, wherein the incubation temperature is about 35° C.

7. The method of claim 6, wherein the activating of the *Chlorella vulgaris* is for at least 90 minutes.

8. The method of claim 7, wherein the microorganism cellular concentration is about $2.5\times10^6$ cells/mL of formulation.

9. The method of claim 5, wherein the bioactive molecule is selected from the group consisting of atrazine, diuron, glyphosate, chlorpyriphos, copper, lead, cadmium, mercury, cyanides, tetracycline, zinc, nickel and ammoniacal nitrogen.

10. The method of claim 5, wherein the incubation under ambient light has a duration of about 10 to 15 minutes.

11. The method of claim 1, wherein the monocellular algae is a *Chlorophyceae*.

12. The method of claim 11, wherein the *Chlorophyceae* is a fresh water *Chlorophyceae*.

13. The method of claim 12, wherein the microorganism cellular concentration is between about $2.5\times10^6$ and $5\times10^6$ cells/mL of formulation.

14. The method of claim 13, wherein the bioactive molecule is selected from the group consisting of atrazine, diuron, glyphosate, chlorpyriphos, copper, lead, cadmium, mercury, cyanides, tetracycline, zinc, nickel and ammoniacal nitrogen.

15. The method of claim 12, wherein the bioactive molecule is selected from the group consisting of atrazine, diuron, glyphosate, chlorpyriphos, copper, lead, cadmium, mercury, cyanides, tetracycline, zinc, nickel and ammoniacal nitrogen.

16. The method of claim 11, wherein the monocellular algae is a marine *Chlorophyceae*.

17. The method of claim 16, wherein the marine *Chlorophyceae* is *Dunalliela tertiolecta*.

18. The method of claim 17, wherein the *Dunalliela tertiolecta* cellular concentration is between about 200,000 and 350,000 cells/mL of formulation.

19. The method of claim 17, wherein the activating of the *Dunalliela tertiolecta* is for at least 45 minutes.

20. The method of claim 19, wherein the bioactive molecule is selected from the group consisting of atrazine, diuron, glyphosate, malathion, chlorpyriphos, progesterone and dicrotophos.

21. The method of claim 1, wherein the microorganism is *Ankistrodesmus falcatus, Monoraphidium arcuatum, Scenedesmus quadricauda, Desmosdesmus subspicatus, Scenedesmus subpicatus, Scenedesmus obliquus, Pseudokirchneriella subspicata* or *Chlamydomonas reinhardtii*.

22. The method of claim 1, wherein the microorganism is a cyanobacteria.

23. The method of claim 22, wherein the cyanobacteria is *Anabaena* sp.

24. The method of claim 23, wherein the activating of the *Anabaena* sp. is for at least 60 minutes.

25. The method of claim 22, wherein the cyanobacteria is *Nostoc commune*.

26. The method of claim 1, wherein the microorganism is *Phaeodactylum tricornutum, Nitzchia clostridium, Lasallia pustulata* or *Zostera caprocorni*.

27. The method of claim 1, wherein the monocellular algae is *Chlorella vulgaris*.

28. The method of claim 27, wherein the formulation further comprises an additive, the additive being i) copper; ii) cadmium; or iii) a combination of copper and cadmium, and wherein the bioactive molecule is a metal ion.

29. The method of claim 28, wherein the incubation temperature is about 35° C.

30. The method of claim 1, wherein said detected fluorescence corresponds to wavelengths higher than 700 nm and said fluorescence is detected following illumination at a wavelength of 475,605 or 660 nm.

31. The method of claim 1, wherein said monocellular algae or cyanobacteria is a stabilized monocellular algae or cyanobacteria.

32. The method of claim 1, wherein the incubation under green light or darkness has a duration of about 10 minutes.

33. The method of claim 1, wherein the incubation under ambient light has a duration of about 10 to 60 minutes.

* * * * *